(12) United States Patent
Schmitt et al.

(10) Patent No.: US 11,660,177 B2
(45) Date of Patent: May 30, 2023

(54) APPLIANCE FOR ASSISTING IN VAGINAL PENETRATION AND PROVIDED TO RECEIVE A WORKING TOOL

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR); Hélène Guyomar, Saint Germain de Martigny (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 288 days.

(21) Appl. No.: 16/954,781

(22) PCT Filed: Dec. 18, 2018

(86) PCT No.: PCT/FR2018/053369
§ 371 (c)(1),
(2) Date: Jun. 17, 2020

(87) PCT Pub. No.: WO2019/122685
PCT Pub. Date: Jun. 27, 2019

(65) Prior Publication Data
US 2021/0085169 A1   Mar. 25, 2021

(30) Foreign Application Priority Data
Dec. 18, 2017  (FR) ...................................... 1762339

(51) Int. Cl.
*A61B 1/303*    (2006.01)
*A61D 19/02*    (2006.01)
(Continued)

(52) U.S. Cl.
CPC ........ *A61D 19/027* (2013.01); *A61B 1/00009* (2013.01); *A61B 1/00045* (2013.01);
(Continued)

(58) Field of Classification Search
CPC ..... A61B 1/00009; A61B 1/05; A61B 1/0676; A61B 1/303; A61B 2503/40; A61D 19/027
(Continued)

(56) References Cited

U.S. PATENT DOCUMENTS 6,447,444 B1 *  9/2002  Avni .................. A61B 1/00151
600/129
2017/0319317 A1  11/2017  Biscay

FOREIGN PATENT DOCUMENTS

FR    2724308 A1    3/1996
WO  2010139912 A1   12/2010
(Continued)

*Primary Examiner* — Christine H Matthews
(74) *Attorney, Agent, or Firm* — Browdyand Neimark, P.L.L.C.

(57) ABSTRACT

An appliance includes a handle, a speculum tube extending axially from the handle as far as a distal end where it has an opening, a video viewing system having a lens arranged in the speculum tube and a transmission device connected to the lens and connectable to a remote viewing screen, and a lens support for keeping the lens in a predetermined position with respect to the speculum tube, in which position the lens is near the opening and opposite the space situated beyond the opening, characterized in that the speculum tube has an end part and a main part extending between the end part and the handle, the end part being arranged around the support and delimiting the opening, the end part being elastically deformable and the main part being rigid.

10 Claims, 5 Drawing Sheets

(51) Int. Cl.
  *A61B 1/00* (2006.01)
  *A61B 1/018* (2006.01)
  *A61B 1/05* (2006.01)

(52) U.S. Cl.
  CPC ............... *A61B 1/018* (2013.01); *A61B 1/05* (2013.01); *A61B 1/303* (2013.01); *A61B 2503/40* (2013.01)

(58) Field of Classification Search
  USPC .......................................................... 600/35
  See application file for complete search history.

(56) References Cited

FOREIGN PATENT DOCUMENTS

| | | | |
|---|---|---|---|
| WO | 2016066962 | A1 | 5/2016 |
| WO | 2017129929 | A1 | 8/2017 |

* cited by examiner

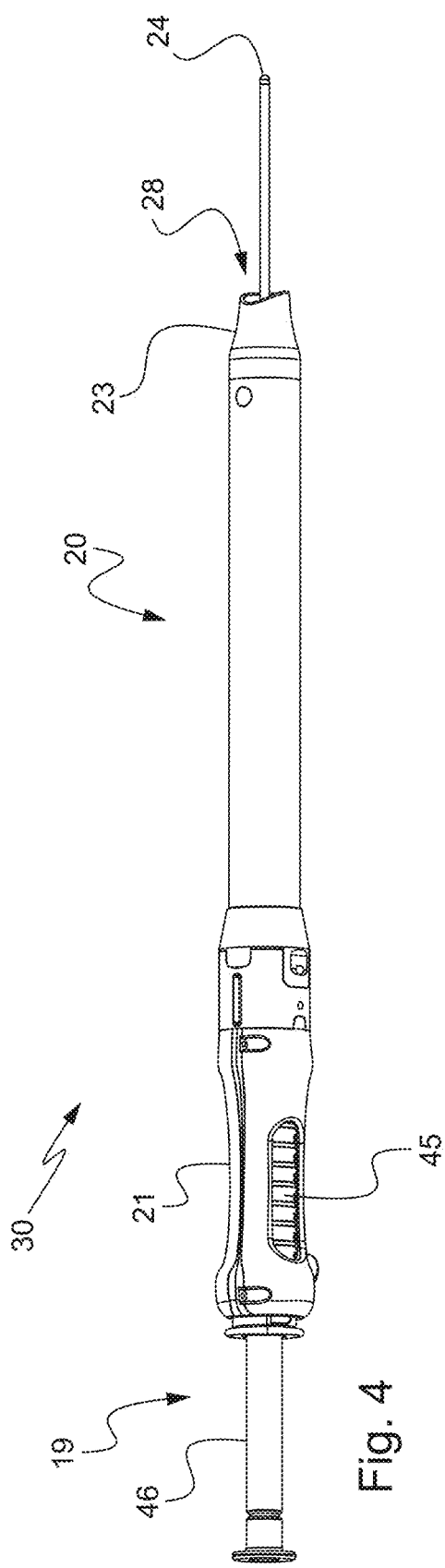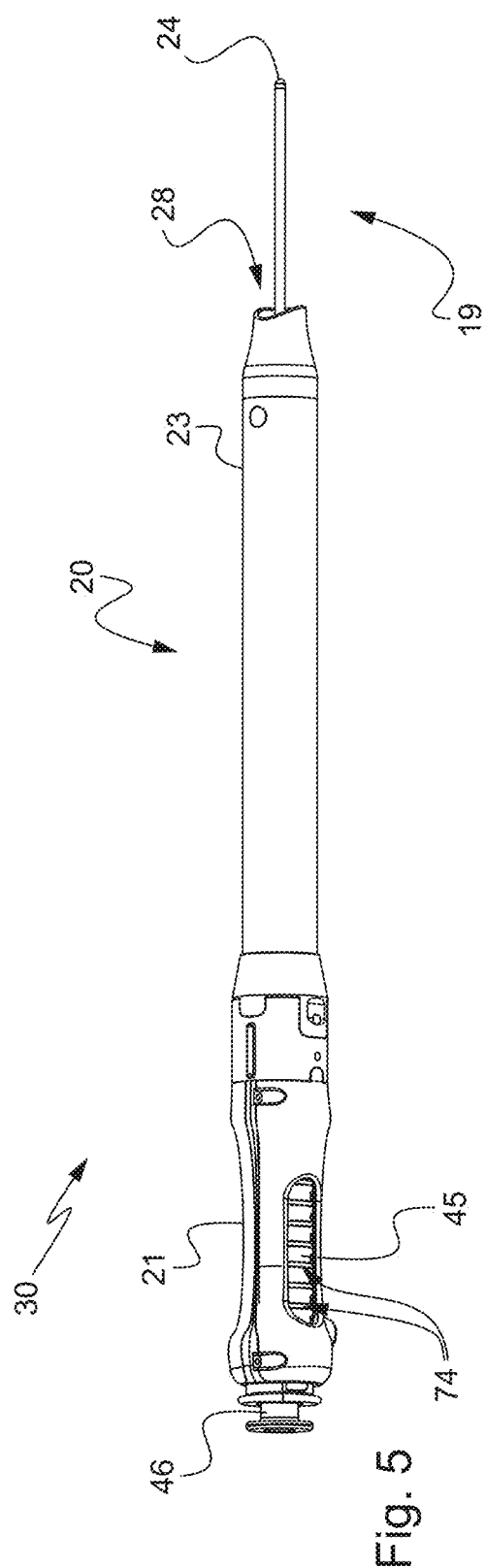

APPLIANCE FOR ASSISTING IN VAGINAL PENETRATION AND PROVIDED TO RECEIVE A WORKING TOOL

FIELD OF THE INVENTION

The invention relates to an apparatus for assisting in vaginal penetration, in particular for farm animals, provided to receive a work tool, in particular an insemination gun to be used with a straw for the preservation of a predetermined dose of liquid-based substance, in particular pure or diluted animal semen.

TECHNOLOGICAL BACKGROUND

From PCT application WO 2016/066962, to which corresponds U.S. patent application US 2017/0319317, there is already known an apparatus for assisting in vaginal penetration which is provided to receive a work tool, comprising a handling shaft and a speculum tube extending axially from the handling shaft to a distal end at which it has an opening. The apparatus further comprises a video viewing system comprising an objective disposed within the speculum tube and a transmission device connected to the objective and connectable to a remotely located screen for viewing the image obtained by the objective. The apparatus also comprises an objective support to hold the objective in a predetermined position relative to the speculum tube in which the objective is in the neighborhood of the opening of the speculum tube and faces the space located beyond that opening.

The handling shaft is furthermore configured to slidingly guide the work tool in the speculum tube such that the work tool can reach an advanced position in which part of the work tool projects beyond the opening of the speculum tube.

To perform an artificial insemination, a work tool is chosen comprising an insemination gun equipped which a straw filed with semen. The speculum tube is inserted into the animal's vagina and once the apparatus is correctly positioned, the tool is pushed towards the advanced position in order for the tip of the sheath of the gun to be inserted through the uterine cervix, then the semen is ejected into the uterus.

Previously, the apparatus (and more specifically the transmission device of the video viewing system) is connected to a remotely located screen such as a smartphone screen. During the operation, the operator is able to observe on the remotely located screen the progression of the speculum tube, then of the insemination gun, thanks to the video viewing system which in real-time sends back the image of the space located beyond the opening of the speculum tube.

SUBJECT OF THE INVENTION

The invention is directed to improving the conditions of use of such an apparatus.

To that end, the invention provides an apparatus for assisting in vaginal penetration provided to receive a work tool, comprising:
- a handling shaft;
- a speculum tube extending axially from the handling shaft to a distal end at which it has an opening;
- a video viewing system comprising an objective disposed within the speculum tube and a transmission device connected to the objective and connectable to a remotely located screen for viewing the image obtained by said objective; and
- an objective support to hold the objective in a predetermined position relative to the speculum tube in which the objective is in the neighborhood of said opening of the speculum tube and faces the space located beyond said opening of the speculum tube;

characterized in that said speculum tube comprises an end part and a main part extending between said end part and said handling shaft, said end part being disposed around said objective support and delimiting said opening, said end part being of elastically deformable material and said main part being of rigid material.

Given that the end part of elastically deformable material surrounds the objective support, which is rigid and rigidly connected (for example via the handling shaft) to the main part of rigid material, the deformations of the end part are limited by the objective support.

Thus, despite its elastically deformable character, the end part cannot deform to the point that its deformations hinder the penetration by the apparatus.

There is thus gained the benefit both of resistance to the deformation which enables the insertion of the end of the speculum tube and of a sufficient deformation capacity for the end part to conform as well as possible to the anatomy of the vagina.

This aptitude of the end part of the speculum tube to resist excessive deformation while being capable of deforming sufficiently to conform to the anatomy of the vagina makes it possible to commence the penetration by the speculum tube as well as possible.

The task of the operator is thus facilitated and the risks of injuries to the animal are reduced, including in difficult anatomical configurations such as the presence of irregularities or protuberances.

According to advantageous features, said end part has an outside surface of which the diameter increases between the opening and the main part.

The fact that the diameter of the outside surface of the end part increases from the opening provides progressiveness which facilitates the insertion of the speculum tube.

The apparatus can thus be used with a greater variety of animals than previously.

The apparatus according to the invention can in particular be used with heifers that have never calved before, or representatives of the buffalo breed such as those of the *Bubalus bubalis* (domestic water buffalo) genus and *Syncerus caffer* (Cape buffalo) genus, in which difficulties of commencing the penetration could only be solved by reducing the diameter of the speculum tube.

According to advantageous features, said end part has an inside surface of which the diameter increases between the opening and the main part and which is contiguous with said objective support.

The end part thus has, starting from the opening, a wall which diverges and which is passed along internally by the objective support, which is thus off-center and inclined towards the opening, which is coaxial with the rest of the speculum tube.

According to advantageous features, the contour of the opening has a least distal zone and a zone which protrudes axially relative to the least distal zone, the least distal zone being at an angular position centered on the objective support.

There is thus gained the benefit both of additional progressiveness on insertion (the axially protruding zone penetrates before the least distal zone) and a field of vision by the objective which is not hindered by the wall of the end part.

According to other advantageous features:
- said apparatus further comprises a guiding support for said tool, said end part being also disposed around said guiding support;
- said objective support and said guiding support form a single part;
- the guiding support comprises a funnel-shaped wall coaxial with the speculum tube and walls each extending from the funnel-shaped wall to an end adjacent the inside surface of the speculum tube; and the objective support comprises a barrel projecting towards the opening from a peripheral zone of the guiding support to a distal end at which it has an opening, said objective being received in the barrel and located at the edge of the opening of the barrel;
- the speculum tube comprises an annular zone in which the main part and the end part overlap;
- in said annular zone, said end part has nipples projecting from its outside surface while the main part has orifices opening onto its inside surface, each said nipple being engaged in a respective orifice; and/or
- in said annular zone, the play between the end part and a wall rigidly connected to said objective support is, opposite at least one said nipple, smaller than the thickness of that nipple.

BRIEF DESCRIPTION OF THE DRAWINGS

The disclosure of the invention will now be continued with the detailed description of an embodiment, given below by way of non-limiting example, with reference to the accompanying drawings. In these:

FIG. 4 is a similar view to FIG. 1 but showing the assembly in an intermediate configuration in which the work tool is in an advanced position on the handling shaft of the apparatus, in which the end of the work tool projects forward from the speculum tube;

FIG. 5 is a similar view to FIG. 4 but showing the assembly in a final configuration in which the semen has been ejected out from the straw and from the work tool;

DETAILED DESCRIPTION OF AN EMBODIMENT

Figure 1:
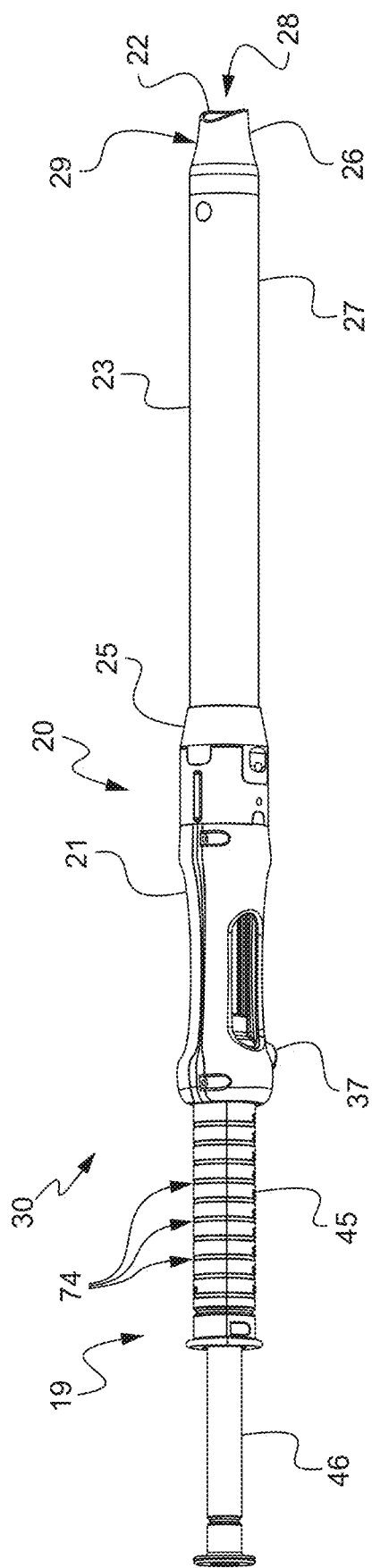
FIG. 1 is a side view of a work assembly comprising an apparatus for assisting in vaginal penetration in accordance with the invention and a work tool partially received in the apparatus, the assembly being in an initial configuration in which the work tool is in a withdrawn position on the handling shaft of the apparatus, in which the end of the work tool is located inside the speculum tube of the apparatus.
Figure 2:
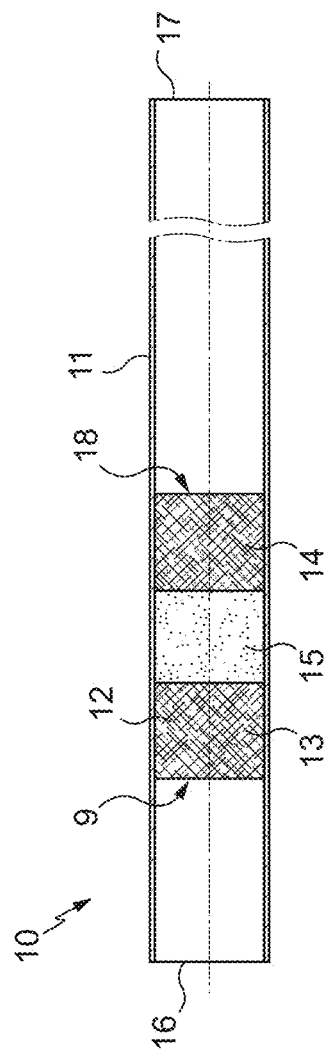
FIG. 2 is a diagrammatic view in longitudinal cross-section of a straw for the preservation of a predetermined dose of liquid-based substance, in particular pure or diluted animal semen, suitable for being used with the work tool.
Figure 3:
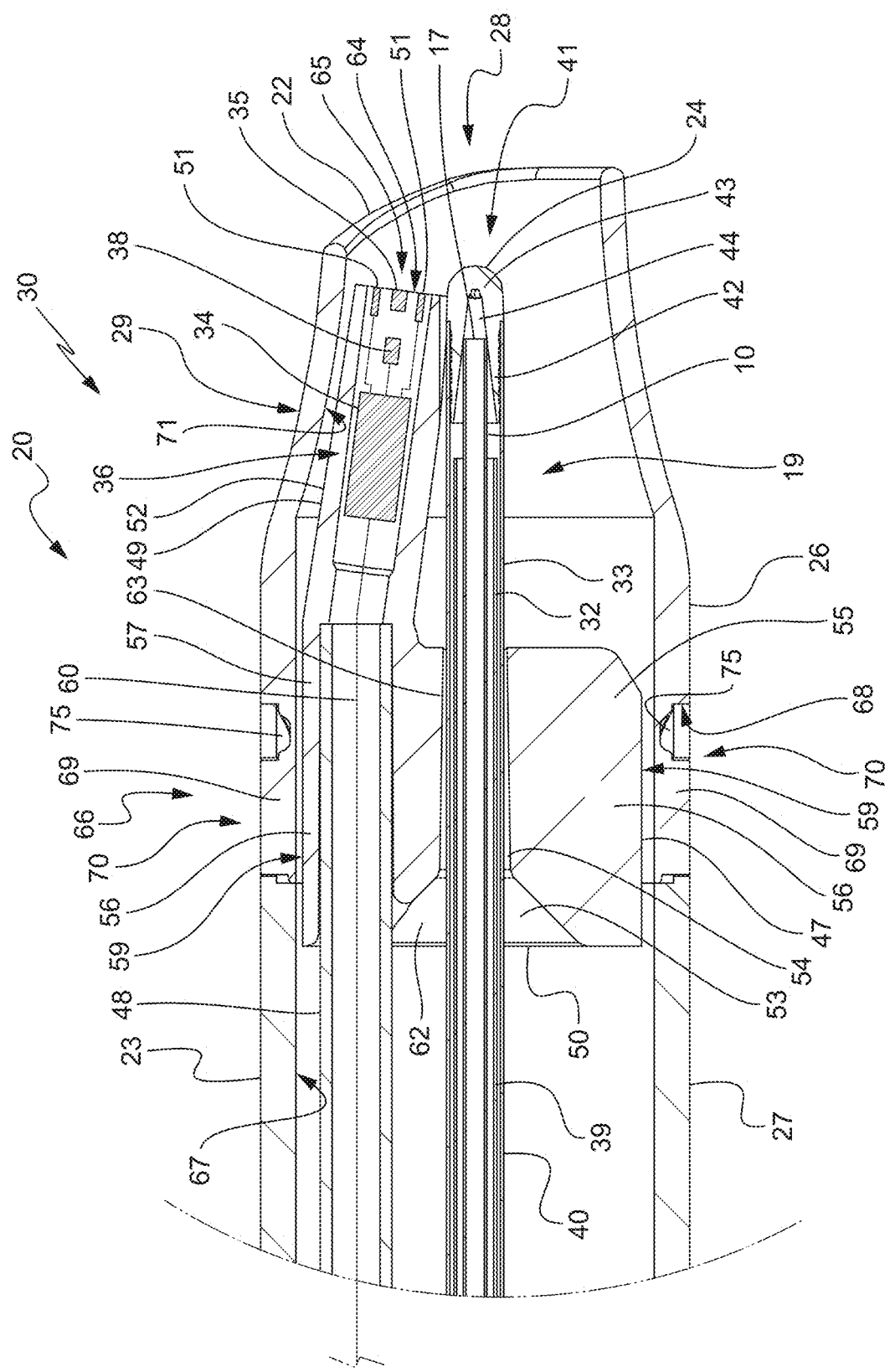
FIG. 3 is a longitudinal section view of the end portion of the assembly which can be seen on the right in FIG. 1, showing the work tool with the preservation straw of FIG. 2 received inside, the video viewing system and a support block configured to slidingly guide the work tool and hold the objective of the video viewing system in a predetermined position.
Figure 6:
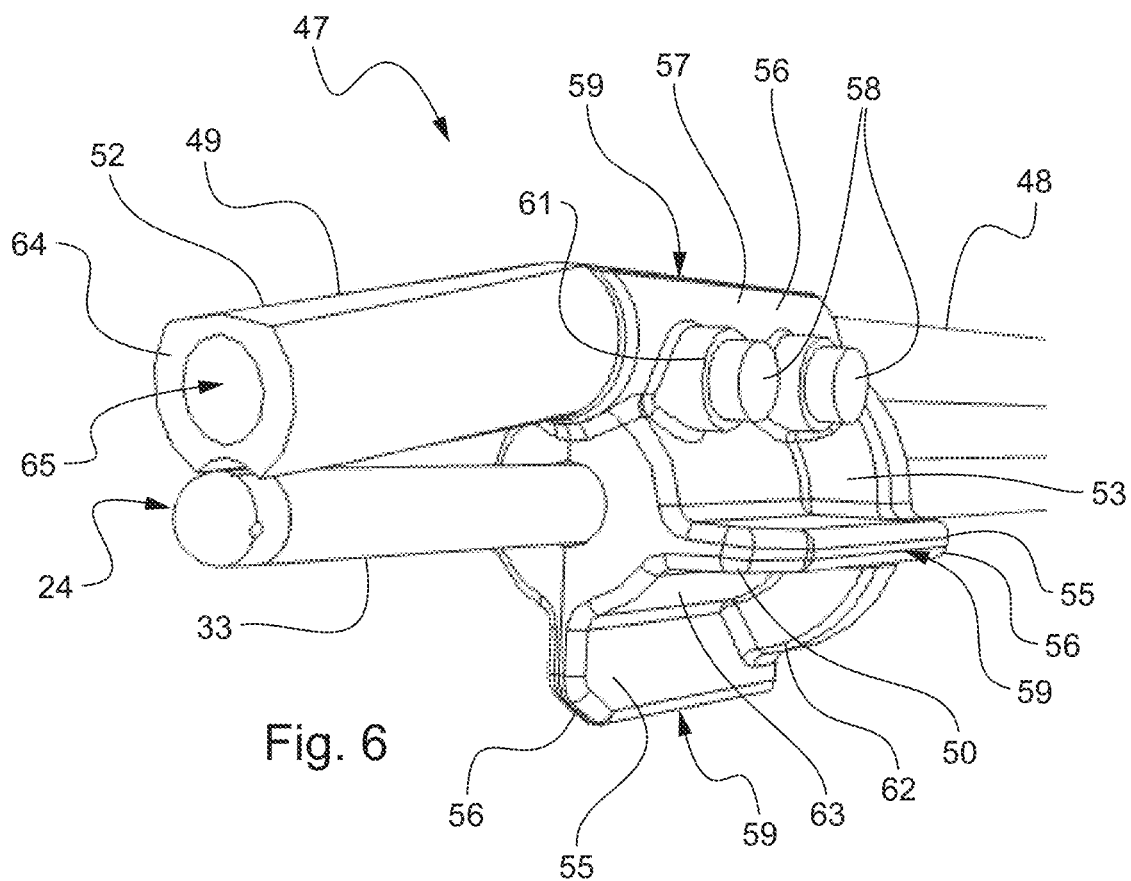
FIG. 6 is a perspective view of the support block in course of cooperation with the work tool, the speculum tube having been removed.
Figure 7:
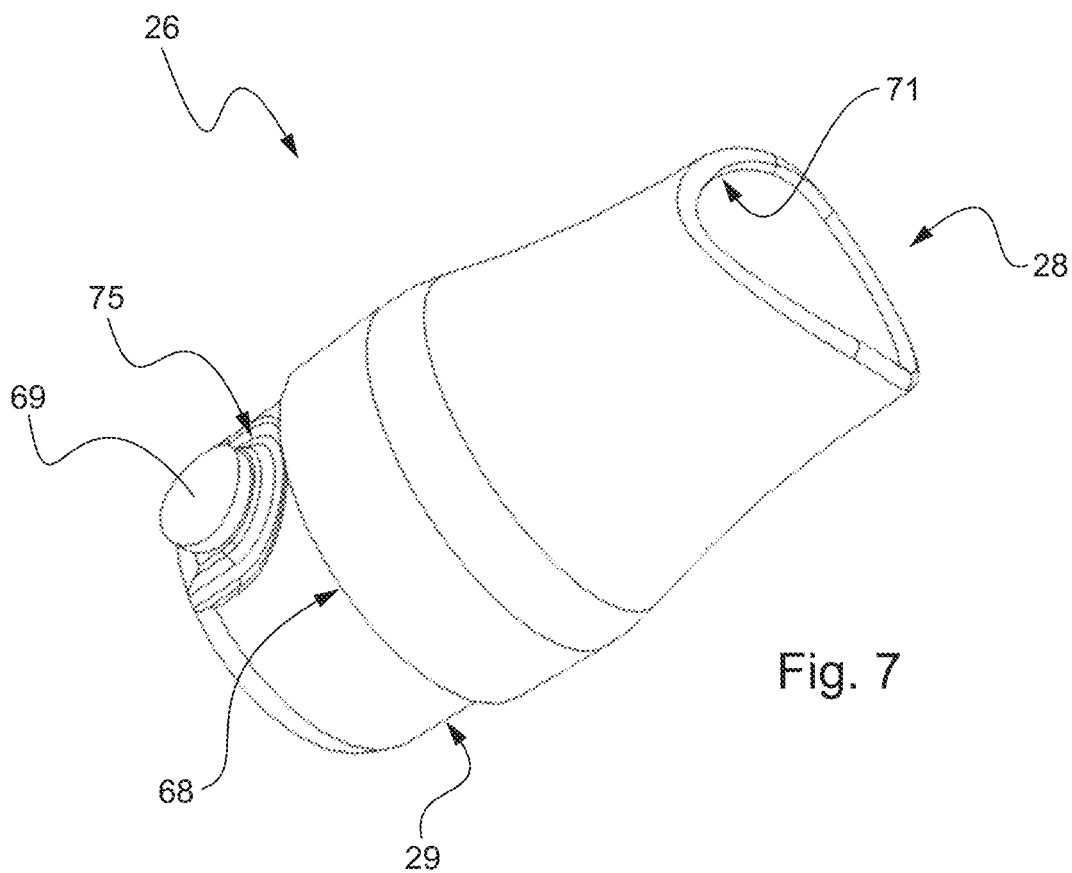
FIGS. 7 to 9 are views of the end part of the speculum tube shown alone and respectively in perspective, then in plan view from above, then in plan view from below.
Figure 8:
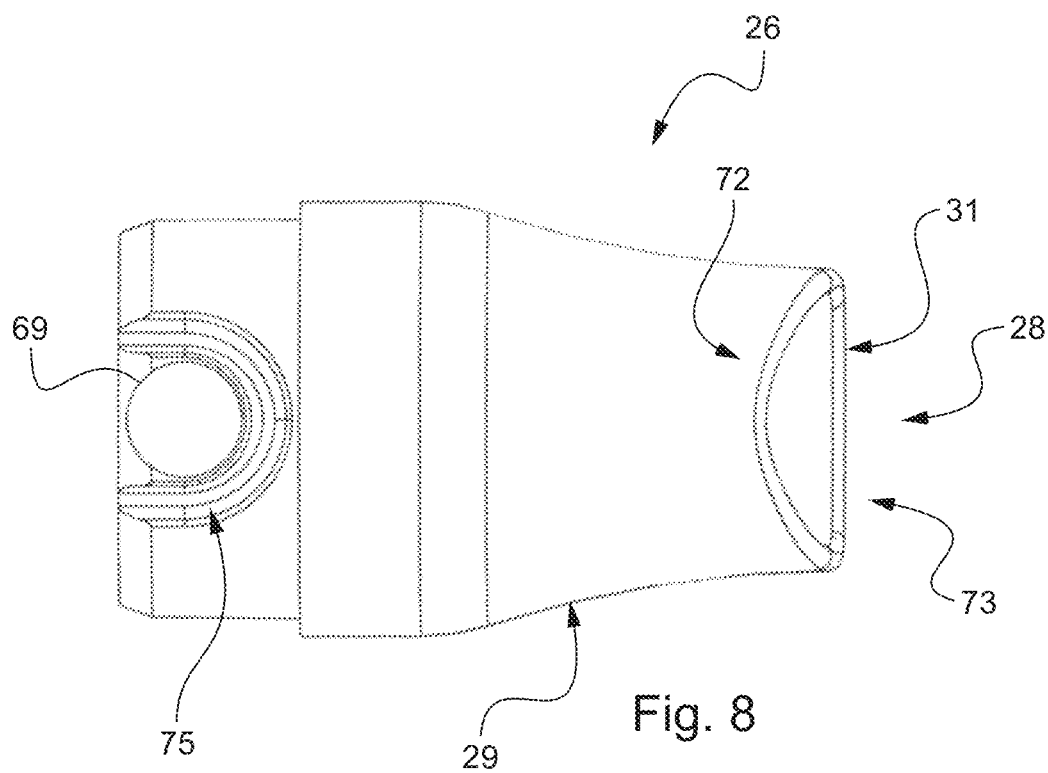
Figure 9:
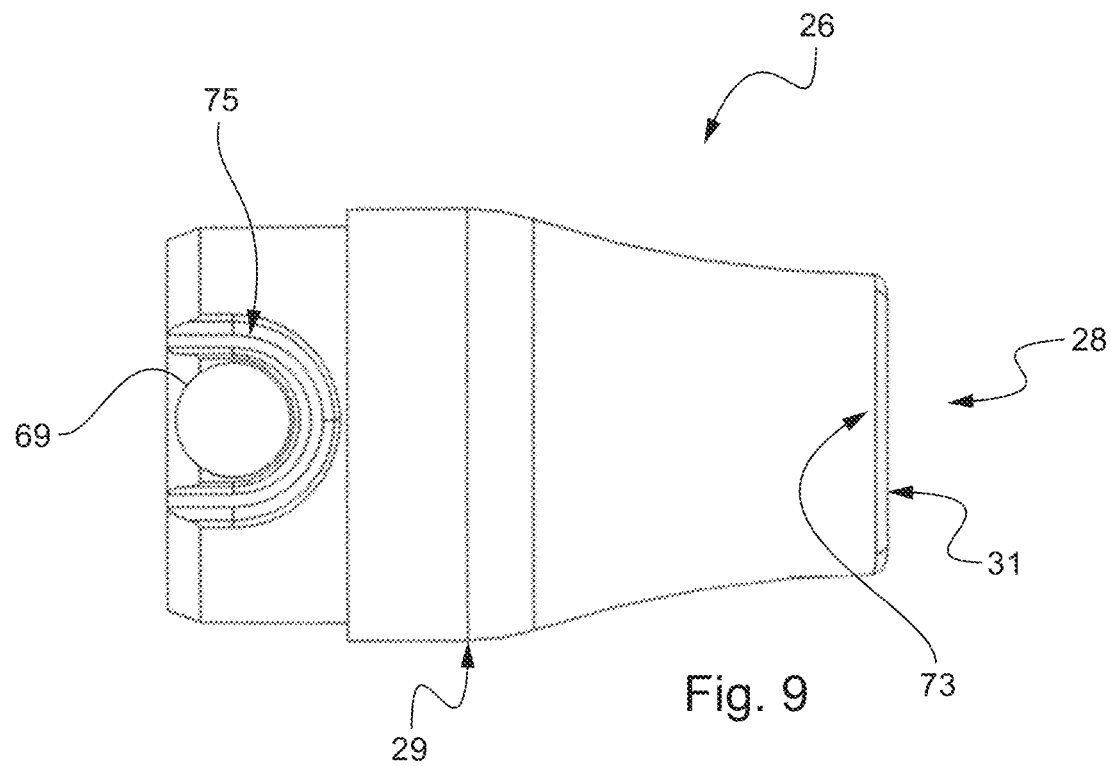

FIGS. 1 to 3 illustrate a work assembly 30 comprising an apparatus 20 for assisting in vaginal penetration, a work tool 19 slidingly received in the apparatus 20 and a straw 10 for preservation of a predetermined dose of liquid-based substance, here pure or diluted animal semen (FIG. 2) which is used with the work tool 19.

The work tool 19 is used here for the artificial insemination of farm animals with the semen contained in the straw 10.

As explained below, the apparatus 20 makes it possible to facilitate the insertion of the work tool 19 into the vagina of the animal and the guiding of the work tool 19 to the uterine cervix, where the semen is to be injected.

The apparatus 20 and the work tool 19 are configured here for cattle.

The apparatus 20 comprises a handling shaft 21 and a speculum tube 23 extending axially from the handling shaft 21 to a distal end 22 at which it has an opening 28.

The handling shaft 21 is formed by a tubular body open at both ends.

The speculum tube 23 is coaxial here to the handling shaft 21.

The apparatus 20 thus has an elongate generally cylindrical shape.

The speculum tube 23 is fastened to the handling shaft 21 via a fastening ring 25.

The ring 25 is fastened in the neighborhood of the proximal end of the speculum tube 23 (the end oriented towards the handling shaft 21), here by bonding.

The fastening ring 25 is attached to the distal end of the handling shaft 21 (the end oriented towards the speculum tube 23), here by snap engagement.

The ring 25 and the handling shaft 21 are configured so that the ring 25 can have its snap engagement with the handling shaft 21 undone, the speculum tube 23 thus being removable.

The speculum tube 23 comprises an end part 26, delimiting the opening 28, and a main part 27 extending between the end part 26 and the handling shaft 21.

In other words, the end part 26 extends between the main part 27 and the distal end 22 of the speculum tube 23 which is also the distal end of the end part 26.

The opening 28 is delimited by a contour 31 corresponding to the edge of the end part 26 located at the distal end 22.

The end part 26 is of elastically deformable material, whereas the main part 27 is of rigid material.

The material of the end part 26 here comprises a thermoplastic elastomer material (or TPE) which has a hardness of about 40 Shore D. Generally, the material of the end part 26 has a hardness comprised between 35 and 45 Shore D.

The material of the end part 26 has an elastic limit extension which is approximately 20% here. Generally, this elastic limit extension can be equal to or greater than approximately 20%.

The end part 26 is formed here as a single part.

The material of the main part 27 here comprises PMMA, which is a transparent rigid thermoplastic material.

It will be noted that the end part 26 has an outside surface 29 of which the diameter increases between the opening 28 and the main part 27.

More specifically, this diameter increases until it reaches the outside diameter of the main part 27 which itself remains constant along the length of the main part 27.

Furthermore, the outside surface 29 increases in diameter such that it has a concave curved profile of which the concavity is oriented towards the outside of the tube 23.

The apparatus 20 further comprises a video viewing system comprising an objective 35 (FIG. 3) disposed within the speculum tube 23 and a transmission device 36 connected to the objective 35 and connectable to a remotely located screen (not illustrated) for viewing the image obtained by the objective 35.

The transmission device 36 comprises an electronic circuit 34, a photosensor 38 connected to the electronic circuit 34, a plug socket 37 and a cable 60 connecting the electronic circuit 34 to the plug socket 37.

The photosensor 38 is disposed behind the objective 35 to receive the image obtained by the latter and is configured to convert that image into an analog signal which is then sent to the electronic circuit 34. The photosensor 38 is of CCD type here.

The cable 60 is configured to convey the analog signal from the electronic circuit 34 to the plug socket 37 which is housed in the wall of the handling shaft 21, to the rear of the latter (that is to say in the neighborhood of the opposite end of the handling shaft to the speculum tube).

The video viewing system further comprises one or more lighting members 51, here LED-based lighting members, connected to the electronic circuit 34. The lighting members 51 are juxtaposed to the objective 35 and disposed on opposite sides thereof.

The cable 60 and the plug socket 37 are each configured here both to convey the analog signal and the energy required for the operation of the electronic circuit 34, of the sensor 38 and of the lighting members 51.

The plug socket 37 is a connector of micro-USB type here.

To simplify the drawings, the electronic circuit 34, the sensor 38, the cable 60, the lighting members 51 and the objective 35 are represented very diagrammatically in FIG. 3.

The remotely located screen here forms part of a smartphone (not illustrated) which is configured to be connected to the transmission device 36 using a suitable cable (not illustrated) connected both to the smartphone and to the plug socket 37.

The apparatus 20 further comprises a support block 47 and a mounting bar 48 each received in the speculum tube 23.

The bar 48 is rigidly fastened by each of its ends to the handling shaft 21 and to the support block 47 respectively, the latter thus occupying a predetermined fixed position in the speculum tube 23.

The bar 48 is tubular here and receives the cable 60. On exiting the bar 48, towards the handling shaft 21, the cable 60 passes through the wall of the handling shaft 21 to reach the plug socket 37.

The support block 47 comprises an objective support 49 and a guiding support 50 for the work tool 19, which here form a single part.

The objective support 49 holds the objective 35 in a predetermined position relative to the speculum tube 23 in which the objective 35 is in the neighborhood of the opening 28 of the speculum tube and faces the space located beyond that opening 28, that is to say the space that extends in line with the tube 23.

The objective support 49 furthermore holds the lighting members 51, which are configured to illuminate the space located beyond the opening 28.

It will be noted that the end part 26 of the speculum tube 23 is disposed around the objective support 49.

The guiding support 50 is configured to guide the sliding of the part of the work tool 19 that is received in the speculum tube 23. The guiding support 50 is furthermore configured in order for the work tool 19 to slidingly move in an axial direction centered relative to the outside surface of the speculum tube 23.

It will be noted that the end part 26 of the speculum tube 23 is also disposed around the guiding support 50.

Generally, the end part 26 of the speculum tube 23 is disposed around the support block 47.

The work tool 19 here comprises an extension 45, a piston 46 slidingly mounted in the extension 45, a re-usable insemination gun 32 and a single-use sanitary sheath 33 (partially illustrated in FIG. 3) which is used with the straw 10 (FIGS. 2 and 3).

The extension 45 is configured to be slidingly mounted in the handling shaft 21 and is provided on its outside surface with a plurality of annular grooves 74 regularly spaced with a predetermined pitch. The annular grooves 74 are configured to cooperate with a bead (not illustrated) provided on the inside surface of the handling shaft 21 so as to form positioning notches for the work tool 19 relative to the apparatus 20. The predetermined pitch is approximately 1 cm here.

The work tool 19 is received in the apparatus 20 with the extension 45 which is slidingly mounted in the handling shaft 21, while the part of the work tool 19 that is received in the speculum tube 23 is able to slide through the guiding support 50.

The work tool 19 is thus mounted movably in terms of translation relative to the apparatus 20 between a position that is withdrawn (FIGS. 1 and 3) relative to the apparatus 20, in which a distal end 24 of the work tool 19 is located inside the speculum tube 23 (that is to say inside the internal space of the tube 23 delimited by its wall), and a position that is advanced relative to the apparatus 20 (FIGS. 4 and 5), in which the distal end 24 of the tool 19 projects forwardly of the speculum tube 23.

In the withdrawn position, the distal end 24 of the tool 19 is thus situated on the same side of the opening 28 as the tube 23, that is to say rearward of the opening 28.

In the advanced position, the distal end 24 of the tool 19 is thus situated on the opposite side of the opening 28 from the tube 23, that is to say forward of the opening 28.

In FIG. 3, the straw 10 can be seen received in the work tool 19.

This straw 10 will be described in more detail with reference to FIG. 2.

The straw 10 illustrated in FIG. 2 comprises a tube 11 and a stopper 12.

The tube 11 is conventionally made from extruded plastic material, with an inside diameter for example of 1.6 or 2.5 mm and a length of the order of 133 mm.

The stopper 12 is usually of the three-part type originally described in French patent 995.878, corresponding to British patent 669,265, i.e. formed by two plugs 13 and 14 made from a fibrous substance enclosing a powder 15 which, on contact with a liquid, is capable of transforming into an impermeable paste or gel adhering to the wall of the tube so that the stopper is liquid-tight.

In the initial state, shown in FIG. 2, the stopper 12 is disposed in the neighborhood of the end 16 of the tube 11 and it is provided that in the filled state, the dose of liquid substance which must be preserved in the straw 10 is disposed between the stopper 12 and the end 17 of the tube 11 that is the furthest from the stopper 12.

In order to fill the straw 10, the end 16 is placed in communication with a vacuum source while the end 17 is placed in communication with a vessel containing the substance to be introduced into the straw.

The air initially contained between the stopper 12 and the end 17 is sucked through the stopper while the substance moves forward in the tube 11 until it encounters the stopper 12, by the end 18 thereof that is turned towards the end 17 of the tube 11, that is to say the end of the stopper 12 that can be seen on the right in FIG. 2.

If necessary, the straw is welded in the neighborhood of one or both of its two ends 16 or 17 and is placed in cold storage.

To empty the straw 10, if necessary after cutting the welded end portions and thawing, there is inserted into the tube 11 a rod which comes to bear on the end 9 of the stopper 12 (which end is situated on the opposite side to the end 18). Using this rod, the stopper 12 is made to slide in the manner of a piston towards the end 17 or the end which corresponds after cutting the welded portion, which causes the expulsion of the dose of substance which had been introduced into the straw.

A description will now be given in more detail of the work tool 19 and of its cooperation with the straw 10.

The insemination gun 32 (FIG. 3) of the work tool 19 comprises a rigid tubular body 39, for receiving the straw 10 filled with semen, and comprises the rod for driving the stopper 12, slidingly mounted in the rigid tubular body 39.

The extension 45 of the work tool 19 is mechanically connected to the rigid tubular body 39 of the gun 32, while the piston 46 is mechanically connected to the rod of the gun 32.

The sliding of the piston 46 relative to the extension 45 thus drives the sliding of the rod relative to the rigid tubular body 39 of the gun 32.

Prior to insertion of the straw 10 into the rigid tubular body 39, the inseminator takes the piston 46 as far as possible out from the extension 45, in order for the rod to be out or withdrawn as far as possible from the body 39 at the proximal end, that is to say at the end which is manipulated by the inseminator during the operation, then the straw 10 is inserted into the rigid tubular body 39 at its distal end (the far end from the proximal end), the straw 10 being inserted with the end 16 of the tube 11 (the end closest to the stopper 12), first. The straw 10 is pushed into the rigid tubular body 39 of the gun 32 until the end 16 of the tube 11 encounters a shoulder forming a pushing-in stop.

The straw 10 is then in place in the rigid tubular body 39 of the gun 32. The end 17 of the tube 11 as well as a certain length of the tube 11 starting from that end remain outside the rigid tubular body 39, that is to say that a certain part of the straw 10 projects beyond the distal end of the rigid tubular body 39 of the gun 32.

The sanitary sheath 33 (FIG. 3) comprises a tube 40 of which the inside diameter is such that the rigid tubular body 39 of the gun 32 may be inserted therein. At one end (the proximal end) the tube 40 of the sanitary sheath 33 is open and at the other end (distal end) the sanitary sheath 33 comprises a tip 41 mechanically connected to the tube 40.

This tip 41 comprises a tail 42 inserted into an end portion of the tube 40 and a head 43 disposed in line with the tube 40.

The tip 41 comprises a duct 44 opening into the tube 40 at the proximal end of the tail 42 (the far end of the tail from the head) and out of the sheath 33 at the outside surface of the head 43.

This internal duct 44 of the tip 41 comprises a portion oriented in the axial direction, narrowing from the proximal end of the tail 42, configured in order that the portion of the tube 11 of the straw 10 situated in the neighborhood of the end 17 (furthest end from the stopper 12) can enter the narrowing portion of the duct 44 and advance to a stop position in which the portion of the tube 11 situated in the neighborhood of the end 17 is clamped around by the wall of that portion of the duct 44.

This clamping round provides at the same time the stop for the pushing-in of the straw 10 into the sheath 33 and the liquid-tightness between the straw 10 and the sheath 33.

The rigid tubular body 39 of the gun 32, in which the straw 10 was placed in advance, is inserted into the sheath 33 by its open end with the straw 10 first, the straw inserts into the duct 44 of the tip 41. The insertion into the sheath 33 ends when the straw 10 comes to bear against the wall of the narrowing duct 44.

The sheath 33 is then fastened to the rigid tubular body 39 of the gun 32, in general in the neighborhood of the proximal end of the sheath 33 (open end of the tube 40) for example with a suitable ring.

The tube 11 of the straw 10 is thus immobilized relative to the assembly formed by the tubular body 39 of the gun 32 and by the sanitary sheath 33 fastened to that body, since the end 16 of the tube 11 bears against the shoulder of the tubular body 39 of the gun 32 and the end 17 bears against the wall of the narrowing portion of the duct 44.

The piston 46 can then be used to drive the rod and make the stopper 12 of the straw 10 slide so as to eject the semen out of the tube 11 and out of the tube 40 of the sheath 33 by the duct 44 which opens outside the sheath 33 at the outside surface of the head 43.

To perform the insemination, the apparatus 20 must of course have been inserted into the animal in advance, then the work tool 19 mounted on the apparatus 20.

The apparatus 20 is inserted into the animal by the inseminator who can monitor the advancement of the speculum tube 23 on the remotely located screen.

It will be noted that the fact that the diameter of the outside surface 29 of the end part 26 increases from the opening 28 provides progressiveness which facilitates the insertion of the speculum tube 23.

Once the apparatus 20 is in place, that is to say when the opening 28 of the tube 23 faces opposite the uterine cervix, the work tool 19 is inserted through the handling shaft 21, the distal end 24 first, and advanced until the extension 45 is pushed into the handling shaft 21 as far as the first notch.

During the insertion of the tool 19, the distal end 24 of the sheath 33 passes entirely through the handling shaft 21, then is inserted into the speculum tube 23 and passes through the guiding support 50.

The assembly 30 then attains the configuration illustrated in FIG. 1, which is an initial configuration in which the work tool 19 is in a withdrawn position relative to the apparatus 20 and the piston 46 is out as far as possible from the extension 45 (the semen not yet having been ejected).

The extension 45 is then pushed forward, notch by notch, to make it slide within the handling shaft 21 until the work tool 19 comes into the advanced position.

During this movement, the distal end 24 of the tool 19 passes through the opening 28 of the tube 23 and advances within the vagina of the animal until it is inserted into the uterine cervix.

The inseminator can monitor the advancement of the distal end 24 on the remotely located screen and thus take care not to injure the animal.

The sliding notch by notch of the extension 45 relative to the handling shaft 21 also makes it possible to control the advancement of the distal end 24.

It will be noted that the objective 35 is maintained by the support 49 in a predetermined position such that the distal end 24 enters into the field of view of the objective 35 (and thus becomes visible on the remotely located screen) before having passed through the opening 28. Thus, so long as the inseminator cannot identify the distal end 24 on the screen, he can be sure that no part of the tool 19 protrudes from the opening 28 and projects into the vagina. As a matter of fact, such a part of the tool 19 protruding from the opening 28 would lead to a risk of injuring the animal at the time of possible uncontrolled movements of the apparatus 20.

It will furthermore be noted that since the work tool 19 is centered relative to the outside surface of the speculum tube 23, it is also centered relative to the vagina. This facilitates the insertion of the tool 19 into the uterine cervix which, too, is centered relative to the vagina.

The assembly 30 then attains the configuration illustrated in FIG. 4, which is an intermediate configuration in which the work tool 19 is in an advanced position and the piston 46 is still out as far as possible from the extension 45.

It then only remains for the inseminator to push the piston 46 to eject the semen and terminate the insemination.

A description will now be given in more detail of the arrangement of the front part of the apparatus 20, at which are located the support block 47 and the end part 26 of the tube 23, with reference to FIGS. 3 and 6 to 9.

The guiding support 50 comprises a funnel-shaped wall 53 coaxial with the speculum tube 23 and walls 56 each extending from the funnel-shaped wall 53 to an end 59 adjacent the inside surface of the speculum tube 23.

The funnel-shaped wall 53 has a conical part 62, oriented towards the handling shaft 21, and a straight part 63 extending from the conical part 62 and oriented towards the opening 28.

The funnel-shaped wall 53 delimits a passage 54 configured to slidingly receive the part of the work tool 19 formed by the sheath 33 and the rigid tubular body 39.

The conical part 62 facilitates the insertion of the sheath 33 into the passage 54 at the time of the insertion of the work tool 19 into the apparatus 20.

The ends 59 of the walls 56 are sufficiently close to the inside surface of the tube 23 for the guiding support 50 to maintain a centered position relative to the inside surface of the speculum tube 23, which is a position at the same time centered relative to the outside surface of the speculum tube 23 since these inside and outside surfaces are concentric.

It will be noted that the walls 56 are each rigidly linked to the objective support 49, here because the guiding support 50 and the objective support 49 are formed as a single part.

The walls 56 here form three fins 55 and a sleeve 57. Two of the three fins 55 are situated at remote opposite locations from each other relative to the funnel-shaped wall 53. Another of the three fins 55 and the sleeve 57 are situated at remote opposite locations from each other relative to the funnel-shaped wall 53.

The fins 55 and/or the sleeve 57 are angularly spaced from each other by approximately a quarter rotation.

The fins 55 each extend in a respective general plane parallel to the speculum tube 23.

The sleeve 57 is generally oriented parallel to the speculum tube 23 and receives internally an end portion of the mounting bar 48. The mounting bar 48 is rigidly fastened here to the support block 47 by screws 58 engaged in chimneys 61 projecting laterally from the wall 56 of the sleeve 57.

It will be noted that the sleeve 57 is located in a peripheral zone of the guiding support 50 and is off-center relative to the speculum tube 23.

The objective support 49 further comprises a barrel 52 projecting towards the opening 28 from a peripheral zone of the guiding support 50 to a distal end 64 at which it has an opening 65.

The objective 35 is received in the barrel 52 and is located at the edge of its opening 65.

It will be noted that here the electronic circuit 34, the photosensor 38 and the lighting members 51 are all received in the barrel 52.

The barrel 52 more specifically extends from the sleeve 57 which it extends, the internal space of the barrel 52 communicating with that of the sleeve 57.

On exiting the bar 48, by the support block 47, the cable 60 passes within the barrel 52 to reach the electronic circuit 34.

It will be noted that the barrel 52 is off-center relative to the speculum tube 23 and that the barrel 52 extends in an inclined direction towards the opening 28 of the speculum tube 23 and towards the inside of the speculum tube 23.

In the front part of the apparatus 20, the speculum tube 23 comprises an annular zone 66 in which the main part 27 and the end part 26 overlap.

The main part 27 has an inside surface 67 which delimits its internal space.

In the annular zone 66, the end part 26 is fitted by insertion into the main part 27 with the outside surface 29 of the end part 26 being in contact with the inside surface 67 of the main part 27.

In the annular zone 66, the outside surface 29 of the end part 26 is set back relative to the part of the outside surface 29 which is outside the annular zone 66.

Due to this, the end part 26 has a shoulder 68 which comes to bear against the transverse end surface of the main part 27 located at its distal end (the end oriented towards the opening 28).

Furthermore, in the annular zone 66, the inside surface 67 of the main part 27 is recessed relative to the part of the inside surface 67 which is outside the annular zone 66.

On account of the respective recessed formations of the outside surface 29 of the end part 26 and of the inside surface 67 of the main part 27 in the annular zone 66, the inside and outside surfaces of the speculum tube 23 remain smooth at the junction between the main and end parts 27 and 26.

It will be noted that in the annular zone 66, the main part 27 and the end part 26 are both disposed around the guiding support 50.

In the annular zone 66, the end part 26 has two nipples 69 projecting from the outside surface 29 while the main part 27 has two orifices 70 opening onto its inside surface 67, each nipple 69 being engaged in a respective orifice 70.

The nipples 69 and the orifices form locking members which oppose both axial movement and rotational movement of the end part 26 relative to the main part 27.

Each orifice 70 furthermore opens onto the outside surface of the speculum tube 23, the surface of the nipple 69 engaged in that orifice 70 being flush with the outside surface of the tube 23.

The two nipples 69 are located at diametrically remote opposite locations from each other on the end part 26; while the two orifices 70 are located at diametrically remote opposite locations from each other on the speculum tube 23.

Furthermore, in the annular zone 66, each of the pairs formed by an orifice 70 and a nipple 69 engaged in the orifice 70, is located angularly opposite a respective wall 56 of the guiding support 50 with, opposite each nipple 69, the play between the end part 26 and the respective wall 56 being smaller than the thickness of that nipple 69.

It is thus impossible for a nipple 69 to disengage from the orifice 70 in which it is received so long as the support block 47, and in particular the guiding support 50, is in place in the tube 23 opposite the annular zone 66. To dismantle the end part 26, the fastening ring 25 must first of all have its snap engagement undone to be able to separate the tube 23 from the handling shaft 21. The tube 23 is then moved apart from the handling shaft 21 such that the block support 47 is no longer located opposite the annular zone 66.

The nipples 69 can then be pressed towards the inside of the tube 23 to be disengaged from the orifices 70.

To facilitate the disengagement and/or engagement of the nipples 69 in the orifices 70, the end part 26 furthermore has U-shaped grooves 75 provided in its outside surface 29 at the foot of each nipple 69 and surrounding the latter.

The end part 26 furthermore has an inside surface 71 of which the diameter increases between the opening 28 and the main part 27, the diameter of the opening 28 being smaller than the inside diameter of the main part 27, and the opening 28 being coaxial with the speculum tube 23.

The diameter of the inside surface 71 increases until it has the same diameter as the inside surface 67 of the main part 27 (outside the annular zone 66).

The inside surface 71 is furthermore contiguous with the barrel 52 of the objective support 49, which is off-center and inclined as already explained.

It will be noted that the wall of the end part 26 is thinner in the part in which its inside and outside surfaces 71 and 29 increase in diameter, than between that part and the shoulder 68. Between this part and the shoulder 68, the wall has the same thickness as the main part 27.

The contour 31 of the opening 28 has a least distal zone 72 and a zone 73 which protrudes axially relative to the least distal zone 72, the least distal zone 72 being at an angular position centered on the objective support 49.

In other words, the contour 31 of the opening 28 is axially closer to the opening 65 of the barrel 52 in the zone 72 than in the zone 73.

The field of vision by the objective 35 is thus not hindered by the wall of the end part 26.

The proximity of the opening 65 of the barrel with the opening 28 of the tube 23 also makes it possible to avoid a portion of the end part 26 that is axially forward of the end 64 of the barrel 52 (and thus not surrounding the barrel 52) folding in front of the objective 35 and obstructing its field of vision, by deforming on insertion of the tube 23 into the animal.

In variants not shown:
the work tool has no insemination gun and comprises for example sampling tweezers, or a listening device;
the sanitary sheath has no tip and instead has a folded rim forming a hem at its distal end and a sliding sleeve disposed inside the sheath, the sleeve being configured to receive an end of the straw and provide sealing between the sheath and the straw when the straw pushes the sleeve to come to bear against the hem.
the video viewing system only comprises a single lighting member juxtaposed against the objective;
the photosensor is not of CCD type but is for example of CMOS type;
the transmission device of the video viewing system has no electronic circuit, no photosensor and no cable but instead comprises an optic fiber cable;
the transmission device has no plug socket to connect thereto a remotely located screen and comprises instead a wireless connection device, for example a radio emitter/receiver of Wi-Fi or Bluetooth type;
the transmission device comprises a projector configured to project the image onto a medium forming the remotely located screen, the medium for example being a wall or a piece of fabric;
the offset screen is not that of a smartphone but that of a tablet, a PC, glasses and/or of a projector;
the fastening ring for fastening the speculum tube to the handling shaft has no snap-engagement members and instead comprises bayonet type fastening members;
the material of the speculum tube is different from a thermoplastic material and is for example of glass;
the speculum tube is not transparent but translucent or opaque;
the end part of the speculum tube has a permanent mechanical connection to its main part, for example by being bonded;
the end part of the speculum tube is not fitted by insertion into its main part but is butt-fitted thereto;
the end part of the speculum tube overlaps its main part on the outside; and/or
the end part/the main part respectively comprise more or fewer than two nipples/orifices, for example three nipples/orifices, each facing a respective wall of the guiding support.

Numerous other variants are possible according to circumstances, and in this connection it is to be noted that the invention is not limited to the examples described and shown.

The invention claimed is:

1. An apparatus for assisting in vaginal penetration provided to receive a work tool, comprising:
a handling shaft;
a speculum tube extending axially from the handling shaft to a distal end of the speculum tube at which the speculum tube has an opening;
a video viewing system comprising an objective disposed within the speculum tube and a transmission device connected to the objective and connectable to a remotely located screen for viewing an image obtained by said objective; and
an objective support to hold the objective in a predetermined position relative to the speculum tube in which the objective is in a neighborhood of said opening of the speculum tube and faces a space located beyond said opening of the speculum tube;
wherein said speculum tube comprises an end part and a main part extending between said end part and said handling shaft, said main part connecting said end part with said handling shaft through a space that separates said end part from said handling shaft, said end part being disposed around said objective support and delimiting said opening, said end part being of elastically deformable material and said main part being of rigid material.

2. Apparatus according to claim 1, wherein said end part has an outside surface of which a diameter increases between the opening and the main part.

3. Apparatus according to claim 2, wherein said end part has an inside surface of which a diameter increases between the opening and the main part and which is contiguous with said objective support.

4. Apparatus according to claim 1, further comprising a guiding support for said tool, said end part being also disposed around said guiding support.

5. Apparatus according to claim 4, wherein said objective support and said guiding support form a single part.

6. Apparatus according to claim 1, wherein the speculum tube comprises an annular zone in which the main part and the end part overlap.

7. An apparatus for assisting in vaginal penetration provided to receive a work tool, comprising:
- a handling shaft;
- a speculum tube extending axially from the handling shaft to a distal end of the speculum tube at which the speculum tube has an opening;
- a video viewing system comprising an objective disposed within the speculum tube and a transmission device connected to the objective and connectable to a remotely located screen for viewing an image obtained by said objective; and
- an objective support to hold the objective in a predetermined position relative to the speculum tube in which the objective is in a neighborhood of said opening of the speculum tube and faces a space located beyond said opening of the speculum tube;
- wherein said speculum tube comprises an end part and a main part extending between said end part and said handling shaft, said end part being disposed around said objective support and delimiting said opening, said end part being of elastically deformable material and said main part being of rigid material; and
- wherein the opening has a contour that has a recessed zone and a zone which protrudes axially relative to the recessed zone, the recessed zone being at an angular position centered on the objective support.

8. An apparatus for assisting in vaginal penetration provided to receive a work tool, comprising:
- a handling shaft;
- a speculum tube extending axially from the handling shaft to a distal end of the speculum tube at which the speculum tube has an opening;
- a video viewing system comprising an objective disposed within the speculum tube and a transmission device connected to the objective and connectable to a remotely located screen for viewing an image obtained by said objective;
- an objective support to hold the objective in a predetermined position relative to the speculum tube in which the objective is in a neighborhood of said opening of the speculum tube and faces a space located beyond said opening of the speculum tube; and
- a guiding support for said tool, said end part being also disposed around said guiding support;
- wherein said speculum tube comprises an end part and a main part extending between said end part and said handling shaft, said end part being disposed around said objective support and delimiting said opening, said end part being of elastically deformable material and said main part being of rigid material;
- wherein said objective support and said guiding support form a single part; and
- wherein the guiding support comprises a funnel-shaped wall coaxial with the speculum tube and extending walls each extending from the funnel-shaped wall to an end of each extending wall adjacent the inside surface of the speculum tube; and the objective support comprises a barrel projecting towards the opening of the speculum tube from a peripheral zone of the guiding support to a distal end of the barrel at which the barrel has an opening, said objective being received in the barrel and located at the edge of the opening of the barrel.

9. An apparatus for assisting in vaginal penetration provided to receive a work tool, comprising:
- a handling shaft;
- a speculum tube extending axially from the handling shaft to a distal end of the speculum tube at which the speculum tube has an opening;
- a video viewing system comprising an objective disposed within the speculum tube and a transmission device connected to the objective and connectable to a remotely located screen for viewing an image obtained by said objective; and
- an objective support to hold the objective in a predetermined position relative to the speculum tube in which the objective is in a neighborhood of said opening of the speculum tube and faces a space located beyond said opening of the speculum tube;
- wherein said speculum tube comprises an end part and a main part extending between said end part and said handling shaft, said end part being disposed around said objective support and delimiting said opening, said end part being of elastically deformable material and said main part being of rigid material;
- wherein the speculum tube comprises an annular zone in which the main part and the end part overlap; and
- wherein in said annular zone, said end part has nipples projecting from an outside surface while the main part has orifices opening onto an inside surface, each nipple being engaged in a respective orifice.

10. Apparatus according to claim 9, wherein in said annular zone, between the end part and a wall rigidly connected to said objective support, there is a gap that is, opposite at least one of said nipples, smaller than the thickness of the at least one of said nipples.

* * * * *